(12) United States Patent
Stadler

(10) Patent No.: US 7,041,307 B2
(45) Date of Patent: *May 9, 2006

(54) BIOCIDE-POLYESTER CONCENTRATES AND BIOCIDAL COMPOSITIONS PREPARED THEREFROM

(75) Inventor: Urs Stadler, Madison, NJ (US)

(73) Assignee: Ciba Specialty Chemicals Corporation, Tarrytown, NY (US)

(*) Notice: Subject to any disclaimer, the term of this patent is extended or adjusted under 35 U.S.C. 154(b) by 191 days.

This patent is subject to a terminal disclaimer.

(21) Appl. No.: 10/199,268

(22) Filed: Jul. 22, 2002

(65) Prior Publication Data

US 2003/0027890 A1    Feb. 6, 2003

Related U.S. Application Data

(63) Continuation of application No. 09/467,809, filed on Dec. 20, 1999, now Pat. No. 6,475,505.

(51) Int. Cl.
*A01N 25/10*    (2006.01)
*A01N 31/16*    (2006.01)

(52) U.S. Cl. ............... 424/409; 424/78.09; 424/78.31; 424/78.37; 424/411; 514/721; 523/122

(58) Field of Classification Search ............... 424/409, 424/411, 78.09, 78.31, 78.37; 523/122; 514/721
See application file for complete search history.

(56) References Cited

U.S. PATENT DOCUMENTS

| 3,991,237 A | * | 11/1976 | Topfl et al. .................. 427/386 |
| 4,663,359 A | | 5/1987 | Rei ............................. 521/85 |
| 4,686,239 A | | 8/1987 | Rei ............................. 521/55 |
| 4,744,976 A | | 5/1988 | Snipes et al. ................ 424/408 |
| 5,229,124 A | | 7/1993 | Rei ............................. 424/409 |
| 5,312,688 A | | 5/1994 | Honguu et al. ............. 428/395 |
| 5,639,803 A | | 6/1997 | Anderson et al. ........... 523/122 |
| 5,702,754 A | | 12/1997 | Zhong ........................ 427/2.12 |
| 5,919,554 A | | 7/1999 | Watterson, III et al. .... 428/201 |
| 5,929,132 A | | 7/1999 | Hani et al. .................. 523/122 |
| 6,013,275 A | * | 1/2000 | Konagaya et al. .......... 424/443 |

FOREIGN PATENT DOCUMENTS

| EP | 0843963 | | 5/1998 |
| GB | 2262468 | | 6/1993 |
| JP | 62000544 | | 1/1987 |
| WO | 92/07031 | | 4/1992 |
| WO | 92/10530 | | 6/1992 |
| WO | WO9724925 | * | 7/1997 |
| WO | 99/27792 | | 6/1999 |
| WO | 00/53413 | | 9/2000 |

OTHER PUBLICATIONS

Patent Abstracts of Japan 08239507 (1996).
Plastics Additives Handbook, 4th Ed., R. Gaechter & H. Mueller, Eds., Hanser Publishers, pp. 10-11 (1993).
Encyclopedia of Chemical Technology, vol. 21, 3rd Ed., John Wiley & Sons, NY, pp. 801-813.
Abstract for JP62000544 (1987).
Hamel, Annu. Tech. Conf., 504, Plast. Eng. 49th, pp. 1897-1900 (1991).

* cited by examiner

*Primary Examiner*—Neil S. Levy
(74) *Attorney, Agent, or Firm*—Tyler A. Stevenson

(57) ABSTRACT

Concentrates of various classical biocides in a polyester carrier resin when incorporated into a substrate resin, preferably a polyolefin such as polypropylene or polyethylene, provide the substrate polymer which biocidal activity with superior resistance to discoloration (yellowing) than when the biocide is directly incorporated into the substrate polymer as a powder at the same total concentration.

8 Claims, No Drawings

BIOCIDE-POLYESTER CONCENTRATES AND BIOCIDAL COMPOSITIONS PREPARED THEREFROM

This is a continuation of application Ser. No. 09/467,809, filed Dec. 20, 1999, now U.S. Pat. No. 6,475,505.

The instant invention pertains to concentrates which comprise a biocidal compound and a polyester carrier resin. The addition of such concentrates into polymer substrates provides biocidal activity to said polymer substrate while preventing discoloration of the substrate.

BACKGROUND OF THE INVENTION

WO 92/07031 teaches the process for preparing a soluble-stable dispersion of a solid biocide comprising a swellable vinyl polymer with a liquid carrier to enable the incorporation of difficultly soluble biocides into polymer resins.

British Patent No. 2,262,468 describes the application of a composition comprising a biocide in a poly(vinyl alcohol) carrier medium to the surface of a mold or former in order to render a plastic acticle biocidally active during the manufacturing process.

Japanese Sho 62-000544 teaches the incorporation of an antibiotic by premixing it with poly(ethylene glycol) or silicone oil and melt blending the pre-mixture into a polyester resin or by preparing a master batch containing the antibiotic in a higher concentration and melting blending the master batch into the polyester.

While the process for putting biocides into plastics by adding the neat active biocidal compound into the polymer substrate during processing or manufacturing is known, this process can lead to discoloration of the final biocidally active substrate. The instant process involves preparing first a biocide-polyester concentrate which is then subsequently added to the polymer substrate. This leads to a final product which is both biocidally active and is resistant to discoloration.

OBJECTS OF THE INVENTION

One object of this invention provides for biocide-polyester concentrates useful for later incorporation into polymer substrates.

Another object of this invention provides for biocidally active polymer compositions resistant to discoloration made by the incorporation of said biocide-polyester concentrate into the polymer.

DETAILED DESCRIPTION

The instant invention pertains to a biocide-polyester concentrate which comprises
  (A) 1–75% by weight of a biocide, and
  (B) 99–25% by weight of a polyester carrier resin.

Preferably, component (A) is 10–50% by weight of a biocide, and component (B) is 90–50% by weight of a polyester carrier resin.

The biocide (A) is at least one compound selected from the group consisting of
  (a) halogenated organic compounds, such as 2,4,4'-trichloro-2'-hydroxydiphenyl ether (IRGASAN® or IRGAGUARD®, Ciba Specialty Chemicals Corp.);
  (b) organosulfur compounds, such as methylene-dithiocyanate, 2-N-octyl-4-isothiazolin-3-one, 3,5-dimethyl-tetrahydro-1,3,5-2H-thiodiazine-2-thione;
  (c) s-triazine compounds, such as 2-methylthio-4-tert-butylamino-6-cyclopropyl-amino-s-triazine;
  (d) copper or copper compounds, such as copper sulfate, copper nitrate, copper-bis(8-hydroxyquinoline);
  (e) organotin compounds, such as tributyltin oxide and its derivatives; and
  (f) bactericides, such as silver and zinc compounds, oxy-bis-phenoxyarsine.

The polyester carrier resin (B) is a homopolyester or a copolyester prepared from aliphatic, cycloaliphatic or aromatic dicarboxylic acids and diols or hydroxycarboxylic acids.

Preferably, the polyester of component (B) has dicarboxylic acid repeat units selected from the group consisting of aromatic dicarboxylic acids having 8 to 14 carbon atoms, aliphatic dicarboxylic acids having 2 to 40 carbon atoms, cycloaliphatic dicarboxylic acids having 6 to 10 carbon atoms, aliphatic hydroxycarboxylic acids having 2 to 12 carbon atoms, aromatic and cycloaliphatic hydroxycarboxylic acids having 7 to 14 carbon atoms, and mixtures thereof.

Preferably such aromatic diacids are terephthalic acid, isophthalic acid, o-phthalic acid, 1,3-, 1,4-, 2,6- and 2,7-naphthalenedicarboxylic acid, 4,4'-biphenyldicarboxylic acid, di(4-carboxyphenyl) sulfone, 4,4'-benzophenonedicarboxylic acid, 1,1,3-trimethyl-5-carboxy-3-(p-carboxyphenyl)indane, di(4-carboxyphenyl) ether, bis(p-carboxyphenyl)methane and bis(p-carboxyphenyl)ethane.

Most preferably, the aromatic diacids are terephthalic acid, isophthalic acid and 2,6-naphthalenedicarboxylic acid.

Suitable aliphatic dicarboxylic acids are linear or branched. Preferably such aliphatic dicarboxylic acids are oxalic acid, malonic acid, succinic acid, glutaric acid, adipic acid, pimelic acid, trimethyladipic acid, sebacic acid, azelaic acid and dimeric acids (products of the dimerization of unsaturated, aliphatic acids such as oleic acid), alkylated malonic acid, alkylated succinic acid, and mixtures thereof.

Suitable cycloaliphatic dicarboxylic acids are 1,3-cyclobutanedicarboxylic acid, 1,3-cyclopentanedicarboxylic acid, 1,3- and 1,4-cyclohexanedicarboxylic acid, 1,3- and 1,4-(dicarboxymethyl)cyclohexane and 4,4'-dicyclohexyldicarboxylic acid.

The diol or glycol portion of the polyester of component (a) are derived from the generic formula HO—R—OH where R is an aliphatic, cycloaliphatic or aromatic moiety of 2 to 18 carbon atoms.

Preferably such diols or glycols are ethylene glycol, diethylene glycol, triethylene glycol, 1,2- and 1,3-propanediol, 1,2-, 1,3-, 2,3- and 1,4-butane-diol, pentane-1,5-diol, neopentane glycol, hexane-1,6-diol, dodecane-1,12-diol, 1,4-cyclohexanedimethanol, 3-methylpentane-2,4-diol, 2-methylpentane1,4-diol, 2,2-diethylpropane-1,3-diol, 1,4-di-(hydroxyethoxy)benzene, 2,2-bis(4-hydroxycyclohexyl)-propane, 2,4-dihydroxy-1,1,3,3-tetramethylcyclobutane, 2,2-bis-(3-hydroxyethoxyphenyl)propane, 2,2-bis-(4-hydroxypropoxyphenyl)ethane, 1,4-dihydroxycyclohexane, p-xylylene glycol, poly(ethylene glycol), poly(propylene glycol), and mixtures thereof.

Preferably, the diol is 1,4-dihydroxycyclohexane, 1,4-cyclohexanedimethanol, ethylene glycol, 1,4-butanediol, 1,2-propylene glycol and 1,3-trimethylene glycol.

Most preferably, the diol is ethylene glycol.

It is furthermore possible for the polyester to be branched by small amounts, for example 0.1 to 3 mol %, based on the dicarboxylic acid present, of monomers having a functionality greater than two, e.g. pentaerythritol, trimellitic acid, 1,3,5-tri(hydroxyphenyl)benzene, 2,4-dihydroxybenzoic acid or 2-(4-hydroxyphenyl-2-(2,4-dihydroxyphenyl)propane.

In the polyester comprising at least two monomers, the polymer can have randomly distributed units or units arranged in the form of blocks.

The polyester of component (B) is preferably poly(ethylene terephthalate) PET, poly(ethylene 2,6-naphthalene-2,6-dicarboxylate) PEN or poly(ethylene/1,4-cyclohexylene-dimethylene terephthalate) PETG copolyester, EASTAR® 6763, Eastman Chemical); most preferably, poly(ethylene terephthalate) or the poly(ethylene/1,4-cyclohexylenedimethylene terephthalate) copolyester.

It is also contemplated that the polyester of component (B) can also be a blend of polyesters or copolyesters including components mentioned above.

The instant invention also pertains to biocidally active polymer compositions resistant to discoloration which comprise
(I) a polymer substrate, and
(II) an effective biocidal amount of a concentrate described above.

The effective biocidal amount of the active component is 0.01 to 5% by weight based on the total composition.

The instant invention also relates to a process for preparing a biocidally active polymer composition, which is resistant to discoloration, which comprises
incorporating into said polymer an effective biocidal amount of a concentrate described above.

The polymer substrate of component (I) is a polyolefin, polystyrene, polyamide, polycarbonate, a polystyrenic such as ABS, SAN, ASA, a nylon (a polyamide), a polyurethane, an acrylate, a polyacrylonitrile a rubber modified styrenic, poly(vinyl chloride), poly(vinyl butyral) or a polyacetal (polyoxymethylene).

Preferably, the polymer substrate is a polyolefin or a polystyrenic, especially polypropylene or polyethylene, most especially linear low density polyethylene (LLDPE), low density polyethylene (LDPE) and high density polyethylene (HDPE).

The incorporation of the instant biocide-polyester concentrate into the polymer substrate affords a number of real advantages over using a neat biocide for the same purpose.

These advantages are
a. better handling;
b. improved industrial hygiene and environmental concerns; and
c. improved control of dosing accuracy for insertion of biocide into the polymer substrate.

Most of all and surprising is the advantage that the use of the biocide-polyester concentrate, when added to a variety of polymer substrates, leads to resistance to discoloration in the biocidally active polymer substrate as compared to the incorporation of neat biocide directly into the polymer substrate.

The following examples are meant for illustrative purposes only and are not to be construed to limit the scope of the instant invention in any way whatsoever.

EXAMPLE 1

Preparation of Biocide-Polyester Concentrate

A commercial poly(ethylene/1,4-cyclohexylenedimethylene terephthalate) PETG copolyester (EASTAR® 6763, Eastman Chemical), is predried in vacuo under nitrogen in an oven at about 70° C. to a moisture level of about 30 ppm as verified on a Mitsubishi VA-O6 moisturemeter. 75 Parts by weight of this dried resin is dry blended with 25 parts by weight of 2,4,4'-trichloro-2'-hydroxydiphenyl ether (IRGASAN® or IRGAGUARD®, Ciba Specialty Chemicals Corp.). The blended resin is then melt compounded under nitrogen into pellets at 180° C. using a Leistritz extruder with corotating, non-intermeshing twin screw at 100 rpm.

EXAMPLE 2

Preparation of Biocidally Active Composition Using a Biocide-Polyester Concentrate Polypropylene homopolymer (PRO-FAX® 6501, Montell Polyolefins, 100 parts), stabilized with 0.05 parts of neopentanetetrayl tetrakis(3,5-di-tert-butyl-4-hydroxyhydrocinnamate), 0.10 parts of tris(2,4-di-tert-butylohenyl) phosphite and 0.05 parts of calcium stearate is dry blended without a biocide; or with 0.25 parts or with 0.50 parts of 2,4,4'-trichloro-2'-hydroxydiphenyl ether (IRGASAN® or IRGAGUARD®, Ciba Specialty Chemicals Corp.) either as a neat powder or as a concentrate as prepared in Example 1. The parts of components are by weight.

These various mixtures are melt compounded in one, two and three passes at two different temperatures [500° F. (260° C.), and 550° F. (288° C.)] in a Superior/MPM extruder using a 24:1 L/D screw with a Maddock mixing head at 80 rpm.

The extruded pellets are compression molded into 125 mil plaques (2"×2", 5.08 cm×5.08 cm) at 450° F. (232° C.) for nine minutes (three minutes at low pressure; three minutes at high pressure; three minutes cooling). Yellowness index (YI) values are determined on the plaques according to ASTM D1925 on a DCI SF600 spectrophotometer. An increase in yellowness corresponds to a positive increase in the YI value.

The results are given in the table below.

| (Biocide % Sample by wt) | Yellowness Index (YI) after multiple pass extrusion at 500° F. (260° C.) | | |
|---|---|---|---|
| | First | Second | Third |
| Control (none) | 7.8 | 9.4 | 14.5 |
| Powder (0.25%) | 8.4 | 8.8 | 9.7 |
| Powder (0.50%) | 8.8 | 9.7 | 9.2 |
| Concentrate (0.25%) | −0.4 | −2.0 | −0.6 |
| Concentrate (0.50%) | −0.1 | −0.2 | 0.0 |

| (Biocide % Sample by wt) | Yellowness Index (YI) after multiple pass extrusion at 550° F. (288° C.) | | |
|---|---|---|---|
| | First | Second | Third |
| Control (none) | 10.4 | 11.9 | 10.4 |
| Powder (0.25%) | 6.4 | 6.3 | 6.6 |
| Powder (0.50%) | 7.1 | 7.2 | 7.4 |
| Concentrate (0.25%) | 0.3 | −2.3 | −0.7 |
| Concentrate (0.50%) | −1.8 | −1.1 | 0.5 |

These results clearly show that the plaques which contain the biocide incorporated therein using the concentrate are far superior in color performance (much lower YI values) than the plaques containing the same concentration of biocide added as a neat powder.

EXAMPLE 3

Preparation of Biocidally Active Composition Comparing a Biocide-Polyester Concentrate with a Biocide-Polyethylene Concentrate Following the general procedure of Example 1, a concentrate of 10% by weight of 2,4,4'-trichloro-2'-hydroxydiphenyl ether (IRGASAN® or IRGAGUARD®, Ciba Specialty Chemicals Corp.) is prepared in low density polyethylene.

Following the general procedure of Example 2, polypropylene homopolymer (100 parts) mixtures without biocide; and with 0.25 and 0.50 parts of the biocide-polyethylene concentrate made above; and with 0.25 and 0.50 parts of the biocide-polyester concentrate made in Example 1. The parts of components are by weight. These mixtures are melt compounded in three passes at 550° F. (288° C.) as seen in Example 2. The extruded pellets are compression molded and the yellowness index (YI) values are determined.

The results are seen in the table below.

| (Biocide % Sample by wt) | Yellowness Index (YI) after multiple pass extrusion at 550° F. (288° C.) | | |
|---|---|---|---|
| | First | Second | Third |
| Control (none) | 8.9 | 8.8 | 12.5 |
| Polyethylene Concentrate (0.25%) | 5.6 | — | 5.0 |
| Polyethylene Concentrate (0.50%) | 9.3 | 11.8 | 10.6 |
| Polyester Concentrate (0.25%) | 0.3 | — | 1.3 |
| Polyester Concentrate (0.50%) | 1.2 | 1.0 | 1.5 |

These results show a far superior performance with regard to color stability of the plaques prepared with the biocide-polyester concentrate as compared to the plaques prepared with the biocide-polyethylene concentrate.

What is claimed is:

1. A biocidally active polymer composition resistant to discoloration which comprises a melt blend of
   (I) a polymer substrate, and
   (II) an effective biocidal amount of a biocide-polyester concentrate,
   wherein the polymer substrate is a polyolefin, polystyrene, polyamide, polycarbonate, a polystyrenic, a polyurethane, an acrylate polymer, a polyacrylonitrile, a rubber modified styrenic polymer, poly(vinyl chloride), poly(vinyl butyral) or a polyacetal,
   which concentrate comprises 10–50% by weight of a biocide and 90–50% by weight of a polyester selected from the group consisting of poly(ethylene terephthalate) PET, poly(ethylene 2,6-naphthalene-2,6-dicarboxylate) PEN and poly(ethylene/1,4-cyclohexylenedimethylene terephthalate) PETG copolyester,
   where the biocide is 0.01 to 5% by weight based on the total composition and
   wherein the biocide is
   (a) 2,4,4'-trichloro-2'-hydroxydiphenyl ether.

2. A composition according to claim 1 wherein the polyester is poly(ethylene terephthalate) or the poly(ethylene/1,4-cyclohexylenedimethylene terephthalate) copolyester.

3. A composition according to claim 1 wherein the polymer substrate is a polystyrenic selected from the group consisting of acrylonitrile/butadiene/styrene copolymer, styrene/acrylonitrile copolymer and acrylate/styrene/acrylonitrile copolymer.

4. A composition according to claim 1 wherein the polymer substrate is a polyolefin or a polystyrenic.

5. A composition according to claim 4 wherein the polyolefin is polypropylene or polyethylene.

6. A composition according to claim 5 wherein the polyolefin is linear low density polyethylene (LLDPE), low density polyethylene (LDPE) or high density polyethylene (HDPE).

7. A composition according to claim 4 wherein the polymer substrate is a polystyrenic.

8. A process for preparing a biocidally active polymer composition, which is resistant to discoloration, which process comprises
   incorporating into a polymer, by melt blending, an effective biocidal amount of a biocide-polyester concentrate,
   wherein the polymer is a polyolefin, polystyrene, polyamide, polycarbonate, a polystyrenic, a polyurethane, an acrylate polymer, a polyacrylonitrile, a rubber modified styrenic polymer, poly(vinyl chloride), poly(vinyl butyral) or a polyacetal,
   which concentrate comprises 10–50% by weight of a biocide and 90–50% by weight of a polyester selected from the group consisting of poly(ethylene terephthalate) PET, poly(ethylene 2,6-naphthalene-2,6-dicarboxylate) PEN and poly(ethylene/1,4-cyclohexylenedimethylene terephthalate) PETG copolyester,
   where the biocide is 0.01 to 5% by weight based on the total composition and
   wherein the biocide is
   (a) 2,4,4'-trichloro-2'-hydroxydiphenyl ether.

* * * * *